(12) United States Patent
Schindler et al.

(10) Patent No.: US 7,910,766 B2
(45) Date of Patent: Mar. 22, 2011

(54) PREPARATION OF AT LEAST ONE PARTIAL OXIDATION AND/OR AMMOXIDATION PRODUCT OF A HYDROCARBON

(75) Inventors: Goetz-Peter Schindler, Mannheim (DE); Otto Machhammer, Mannheim (DE); Klaus Joachim Mueller-Engel, Stutensee (DE); Claus Hechler, Ludwigshafen (DE); Jochen Petzoldt, Mannheim (DE); Christoph Adami, Weinheim (DE); Klaus Harth, Altleiningen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1293 days.

(21) Appl. No.: 10/813,010

(22) Filed: Mar. 31, 2004

(65) Prior Publication Data

US 2004/0199001 A1    Oct. 7, 2004

Related U.S. Application Data

(60) Provisional application No. 60/476,166, filed on Jun. 6, 2003.

(30) Foreign Application Priority Data

Apr. 7, 2003 (DE) .................................. 103 16 039

(51) Int. Cl.
*C07C 253/08* (2006.01)
*C07C 255/06* (2006.01)
*C07C 51/16* (2006.01)

(52) U.S. Cl. .......................... 558/320; 558/466; 562/545

(58) Field of Classification Search .................. 558/320, 558/466; 562/545
See application file for complete search history.

(56) References Cited

U.S. PATENT DOCUMENTS

| 3,161,670 A | 12/1964 | Adams et al. |
| 5,550,309 A * | 8/1996 | Maunders et al. ............ 585/654 |

FOREIGN PATENT DOCUMENTS

| DE | 33 13 573 | 10/1983 |
| DE | 101 31 297 | 1/2003 |
| DE | 102 11 275 | 9/2003 |
| DE | 102 19 685 | 11/2003 |
| DE | 102 19 686 | 11/2003 |
| EP | 0 117 146 | 8/1984 |
| EP | 0 193 310 | 9/1986 |
| EP | 0 731 077 | 9/1996 |
| EP | 0938 463 B1 * | 6/2002 |
| GB | 2 118 939 | 11/1983 |

* cited by examiner

*Primary Examiner* — James O. Wilson
*Assistant Examiner* — Ebenezer Sackey
(74) *Attorney, Agent, or Firm* — Oblon, Spivak, McClelland, Maier & Neustadt, L.L.P.

(57) ABSTRACT

A process for preparing at least one partial oxidation and/or ammoxidation product of a hydrocarbon by partially dehydrogenating at least one saturated hydrocarbon H under heterogeneous catalysis and using the resulting product gas mixture A, which comprises the partially dehydrogenated hydrocarbon H, as such or in modified form for heterogeneously catalyzed partial oxidation and/or ammoxidation of the partially dehydrogenated hydrocarbon present in the product gas mixture A, said process including at least one mechanical separating operation inserted between the product gas mixture A and the heterogeneously catalyzed partial oxidation and/or ammoxidation.

23 Claims, No Drawings

PREPARATION OF AT LEAST ONE PARTIAL OXIDATION AND/OR AMMOXIDATION PRODUCT OF A HYDROCARBON

BACKGROUND OF THE INVENTION

1. Field of the Invention

The present invention relates to a process for preparing at least one partial oxidation and/or ammoxidation product of a hydrocarbon by subjecting at least one saturated hydrocarbon H to a heterogeneously catalyzed dehydrogenation in the gas phase to form a product gas mixture A which comprises at least one partially dehydrogenated hydrocarbon H, leaving constituents present in the product gas mixture A, other than the saturated hydrocarbon H and other than the partially dehydrogenated hydrocarbon H therein, or partly or fully removing them to obtain a product gas mixture A', and subjecting product gas mixture A and/or product gas mixture A', as a constituent of a gas mixture B, to at least one heterogeneously catalyzed partial oxidation and/or ammoxidation of the at least one partially dehydrogenated hydrocarbon H present in the product gas mixture A and/or product gas mixture A'.

2. Description of the Background

In this document, a heterogeneously catalyzed dehydrogenation refers to a dehydrogenation which proceeds endothermically and in which the primary by-product formed is hydrogen. It is carried out over solid catalysts which reduce the activation energy required for the thermal cleavage of a C—H bond. The heterogeneously catalyzed dehydrogenation differs from a heterogeneously catalyzed oxydehydrogenation in that the latter is forced by oxygen present and water is formed as the primary by-product. In addition, a heterogeneously catalyzed oxydehydrogenation proceeds exothermically.

In this context, a complete oxidation of a hydrocarbon means that all of the carbon present in this hydrocarbon is converted to oxides of carbon (CO, $CO_2$).

Reactions with oxygen which deviate from this are partial oxidations and, in the presence of ammonia, partial ammoxidations.

The process described at the outset is known (cf., for example, DE-A 10219686, DE-A 10246119, DE-A 10245585, DE-A 10219685, EP-A 731077, DE-A 3313573, DE-A 10131297, DE-A 10211275, EP-A 117146, GB-A 2118939, U.S. Pat. No. 4,532,365, U.S. Pat. No. 3,161,670 and EP-A 193310) and is employed, inter alia, for preparing acrolein, acrylic acid and/or acrylonitrile from propane, methacrolein, methacrylic acid and/or methacrylonitrile from isobutane. The partial ammoxidation differs from the partial oxidation essentially by the presence of ammonia in the reaction mixture. Suitable choice of the ratio of $NH_3$ and $O_2$ can allow partial oxidation and partial ammoxidation also to be carried out in parallel, i.e. simultaneously. Addition of inert diluent gases keeps the reaction mixture of the partial oxidation and/or ammoxidation outside the explosion range.

In this process (in particular in accordance with the teaching of DE-A 3313573, EP-A 117146, GB-A 2118939, U.S. Pat. No. 4,532,365 and U.S. Pat. No. 3,161,670), either product gas mixture A as such and/or product gas mixture A', as a constituent of a gas mixture B, can be subjected to at least one heterogeneously catalyzed partial oxidation and/or ammoxidation of the at least one partially dehydrogenated hydrocarbon H present in the product gas mixture A and/or product gas mixture A'.

In the simplest case, the product gas mixture A can be converted to the product gas mixture A' by partly or fully removing any steam present in the product gas mixture A. This can be effected, for example, by cooling the product gas mixture and partly or fully condensing out any steam present in it.

It will be appreciated that other constituents present in the product gas mixture A can also be removed to obtain a product gas mixture A'. For example, the product gas mixture A can be passed through a membrane, generally configured as a tube, which is permeable only for hydrogen present in the product gas mixture A, thus partly or fully removing hydrogen present in the product gas mixture A. $CO_2$ present in the product gas mixture A can be removed by conducting the product gas mixture A through an aqueous alkali solution. An alternative removal method is absorption/desorption (stripping) according to DE-A 10245585.

However, a disadvantage of the prior art processes is that neither the product gas mixture A nor the product gas mixture A' nor the gas mixture B, before the at least one heterogeneously catalyzed partial oxidation and/or ammoxidation, is subjected to a mechanical separating operation by which solid particles present in these gas mixtures can be removed from these gas mixtures. When an absorptive separating process is employed, the absorbent in some cases becomes saturated over time with solid particles. For example, in the course of stripping and/or desorbing, they can be entrained.

As a long-term in-house experiment found, surprisingly, this is disadvantageous in that, in the processes described at the outset, very fine particles of the solid catalyst this is disadvantages in that used for the heterogeneously catalyzed dehydrogenation can be conveyed into the subsequent heterogeneously catalyzed partial oxidation and/or ammoxidation, where they in some cases settle in the fixed catalyst bed used there.

The latter is disadvantageous in that a heterogeneously catalyzed partial oxidation and/or ammoxidation, relative to the reaction stoichiometry, is normally carried out in the presence of an excess of oxygen.

In the presence of oxygen, catalysts suitable for a heterogeneously catalyzed dehydrogenation normally also catalyze complete combustion of hydrocarbons to $CO_2$ and $H_2O$ (cf., for example, U.S. Pat. No. 4,788,371) and the hydrogen-oxygen gas reaction of $H_2$ with $O_2$ to give $H_2O$. Both of these are disadvantageous in that they lead either in an undesired manner to undesired reactant consumption in the heterogeneously catalyzed partial oxidation and/or ammoxidation (which at the same times means, undesirably, additional heat formation) or harbors risks which can only be estimated with difficulty.

SUMMARY OF THE INVENTION

It is an object of the present invention to provide a more advantageous procedure which is suitable in particular for safe continuous operation over comparatively long periods (the on-stream time of catalysts for heterogeneously catalyzed partial oxidations and/or ammoxidations is generally a few years).

We have found that this object is achieved by a process for preparing at least one partial oxidation and/or ammoxidation product of a hydrocarbon by subjecting at least one saturated hydrocarbon H to a heterogeneously catalyzed dehydrogenation in the gas phase to form a product gas mixture A which comprises at least one partially dehydrogenated hydrocarbon H, leaving constituents present in the product gas mixture A, other than the saturated hydrocarbon H and other than the partially dehydrogenated hydrocarbon H therein, or partly or fully removing them to obtain a product gas mixture A', and subjecting product gas mixture A and/or product gas mixture A', as a constituent of a gas mixture B, to at least one heterogeneously catalyzed partial oxidation and/or ammoxidation of the at least one partially dehydrogenated hydrocarbon H present in the product gas mixture A and/or product gas mixture A', which comprises subjecting the product gas mixture A, the product gas mixture A' and/or the gas mixture B, before the at least one heterogeneously catalyzed partial oxidation and/or ammoxidation, to at least one mechanical separating operation by which solid particles present in these gas mixtures can be removed.

DETAILED DESCRIPTION OF THE PREFERRED EMBODIMENTS

The process according to the invention is advantageous in particular when, in the process for heterogeneously catalyzed partial oxidation and/or ammoxidation, product gas mixture A is used as such and/or product gas mixture A' is used which is obtained from product gas mixture A by partly or fully condensing out steam which is generally present therein.

Gas purification apparatus which employs a mechanical separating operation and is suitable in accordance with the invention is, for example, chamber separators, impingement separators and centrifugal separators, which utilize mass forces. However, it is also possible to employ acoustic separators for the process according to the invention. Preference is given to aerocyclones. However, in a simple manner, the mechanical separating operation used in accordance with the invention may also be filtering. Useful filter layers include filter fabrics, porous filter compositions, paper web or oil-wetted metal filters. Electrostatic separators can also be employed in accordance with the invention. In the simplest manner, the gas mixture can even flow through an inert fixed bed in which very fine solid particles present in the gas mixture separate before the gas mixture reaches the catalyst for the heterogeneously catalyzed partial oxidation and/or ammoxidation. In this document, the term "mechanical separating operation" is also intended to include spray apparatus in which the gas is exposed in cocurrent or in countercurrent to liquid droplets (for example of high-boiling organic liquids or of water) which are capable of absorbing solid particles present in the gas. The spray liquid is exchanged after a few recirculations, in order to prevent saturation with solid particles.

It will be appreciated that different mechanical separating operations connected in series can also be used in accordance with the invention.

Generally, the heterogeneously catalyzed dehydrogenation of the saturated hydrocarbon H is carried out in accordance with the invention (especially in the case of propane and/or isobutane) as described in DE-A 3313973, WO 01/96270, DE-A 10131297 or DE-A 10211275.

Since the heterogeneously catalyzed dehydrogenation reaction proceeds with decreasing volume, the conversion can be increased by reducing the partial pressure of the products. This can be achieved in a simple manner, for example by dehydrogenating under reduced pressure and/or by mixing in substantially inert diluent gases, for example steam, which normally constitutes an inert gas for the dehydrogenation reaction. A further advantage which generally results from dilution with steam is reduced carbonization of the catalyst used, since the steam reacts with carbon formed by the principle of coal gasification. Steam can also be used as a diluent gas in the downstream at least one oxidation and/or ammoxidation zone. However, steam can also be removed in a simple manner partly or fully from the product mixture A of the dehydrogenation (for example by condensing), which opens up the possibility, when further using the product mixture A' obtainable here in the at least one partial oxidation and/or ammoxidation, of increasing the proportion of the diluent gas $N_2$. Further diluents suitable for the heterogeneously catalyzed dehydrogenation are, for example, CO, methane, ethane, $CO_2$, nitrogen and noble gases such as He, Ne and Ar. All diluents mentioned can be used either alone or in the form of highly differing mixtures. It is advantageous that the diluents mentioned are generally also suitable diluents in the at least one partial oxidation and/or ammoxidation. Inert diluents are in particular diluents which behave inertly in the particular reaction (i.e. those of which less than 5 mol %, preferably less than 3 mol % and even better less than 1 mol %, is chemically changed). In principle, useful catalysts for the heterogeneously catalyzed dehydrogenation are all dehydrogenation catalysts disclosed by the prior art. They can be divided roughly into two groups, i.e. into those which are of oxidic nature (for example chromium oxide and/or aluminum oxide) and into those which consist of at least one generally comparatively noble metal (for example platinum, palladium, tin, gold, silver) deposited on a generally oxidic support.

In other words, in accordance with the invention, all dehydrogenation catalysts can be used which are recommended in WO 01/96270, EP-A 731077, DE-A 10211275, DE-A 10131297, WO 99/46039, U.S. Pat. No. 4,788,371, EP-A-0 705 136, WO 99/29420, U.S. Pat. No. 4,220,091, U.S. Pat. No. 5,430,220, U.S. Pat. No. 5,877,369, EP-A-0 117 146, DE-A 199 37 196, DE-A 199 37 105 and DE-A 199 37 107. In particular, any of the catalysts according to example 1, example 2, example 3 and example 4 of DE-A 199 37 107 can be used.

These are dehydrogenation catalysts which contain from 10 to 99.9% by weight of zirconium dioxide, from 0 to 60% by weight of aluminum oxide, silicon dioxide and/or titanium dioxide and from 0.1 to 10% by weight of at least one element of the first or second main group, of an element of the third transition group, of an element of the eighth main group of the Periodic Table of the Elements, lanthanum and/or tin, with the proviso that the sum of the percentages by weight is 100% by weight.

To carry out the heterogeneously catalyzed dehydrogenation according to the invention, useful reactor types and process variants are in principle all of those disclosed in the prior art. Descriptions of such process variants are contained, for example, in all prior art documents cited with regard to the dehydrogenation catalysts.

A comparatively comprehensive description of dehydrogenation processes which are suitable in accordance with the invention is also contained in "Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.

It is characteristic of the partial heterogeneously catalyzed dehydrogenation of saturated hydrocarbons that it proceeds endothermically. This means that the heat (energy) required for the attainment of the required reaction temperature has to be fed to the starting reaction gas mixture either before and/or in the course of the heterogeneously catalyzed dehydrogenation.

In addition, it is typical of heterogeneously catalyzed dehydrogenations of saturated hydrocarbons such as propane and isobutane, as a consequence of the high reaction temperatures required, that high molecular weight organic compounds having a high boiling point, up to and including carbon, are formed in small amounts and are deposited on the catalyst surface, thus deactivating it. In order to minimize this disadvantageous accompanying phenomenon, the reaction gas mixture which contains the saturated hydrocarbon H to be dehydrogenated and is to be passed at elevated temperature over the catalyst surface for heterogeneously catalyzed dehydrogenation can be diluted with steam. Depositing carbon is partly or fully eliminated under the conditions given in this way by the principle of coal gasification.

Another possibility for eliminating deposited carbon compounds is to allow an oxygen-containing gas to flow through the dehydrogenation catalyst from time to time at elevated temperature and thus to effectively burn off the deposited hydrocarbon. However, substantial suppression of the formation of carbon deposits is also possible by adding molecular hydrogen to the saturated hydrocarbon H to be dehydrogenated under heterogeneous catalysis (e.g. propane or isobutane) before it is conducted over the dehydrogenation catalyst at elevated temperature.

It will be appreciated that the possibility also exists of adding steam and molecular hydrogen in a mixture to the saturated hydrocarbon H to be dehydrogenated under heterogeneous catalysis. Addition of molecular hydrogen to the heterogeneously catalyzed dehydrogenation of propane also reduces the undesired formation of allene (propadiene), propyne and acetylene as by-products.

A suitable reactor type for the heterogeneously catalyzed dehydrogenation according to the invention is the fixed bed tube or tube bundle reactor. This means that the dehydrogenation catalyst is disposed in one or in a bundle of reaction tubes as a fixed bed. The reaction tubes are heated by a gas, for example a hydrocarbon such as methane, being combusted in the space surrounding the reaction tubes. It is favorable to apply this direct form of catalyst tube heating only to the first about 20 to 30% of the fixed bed and to heat the remaining bed length to the required reaction temperature by the radiated heat released in the course of the combustion. In this way, approximately isothermal reaction control is achievable. Suitable reaction tube internal diameters are from about 10 to 15 cm. A typical dehydrogenation tube bundle reactor comprises from 300 to 1000 reaction tubes. The temperature in the reaction tube interior varies within the range from 300 to 700° C., preferably within the range from 400 to 700° C. Advantageously, the starting reaction gas mixture is fed to the tubular reactor preheated to the reaction temperature. It is possible that the product gas mixture leaves the reaction tube with a temperature which is from 50 to 100° C. lower. However, this exit temperature may also be higher or at the same level. In the context of the aforementioned procedure, it is appropriate to use oxidic dehydrogenation catalysts based on chromium oxide and/or aluminum oxide. Frequently, no diluent gas will be used, but rather the starting materials used for the starting reaction gas will essentially be solely saturated hydrocarbon H (e.g. propane or crude propane). The dehydrogenation catalyst too is usually employed undiluted.

On the industrial scale, a plurality of (e.g. three) such tube bundle reactors can be operated in parallel. In this case, two of these reactors may, in accordance with the invention, optionally be in the process of dehydrogenation, while the catalyst charge in a third reactor is regenerated, without the operation in the at least one partial zone suffering.

Such a procedure is appropriate, for example, in the Linde propane dehydrogenation process disclosed in the literature. However, it is significant for the invention that it is sufficient to use such a tube bundle reactor.

Such a procedure can also be used in the "steam active reforming (STAR) process" which has been developed by Phillips Petroleum Co. (see, for example, U.S. Pat. No. 4,902,849, U.S. Pat. No. 4,996,387 and U.S. Pat. No. 5,389,342).

The dehydrogenation catalyst used in the STAR process is advantageously platinum containing promoters on zinc (magnesium) spinel as the support (see, for example, U.S. Pat. No. 5,073,662). In contrast to the BASF-Linde propane dehydrogenation process, propane to be dehydrogenated is diluted with steam in the STAR process. A typical molar ratio of steam to propane is in the range from 4 to 6. The starting reactor pressure is frequently from 3 to 8 atm and the reaction temperature is advantageously selected from 480 to 620° C. Typical liquid hourly space velocities (LHSV) with the total reaction gas mixture are from 0.5 to 10 $h^{-1}$.

The heterogeneously catalyzed dehydrogenation according to the invention may also be effected in a moving bed. For example, the moving catalyst bed may be accommodated in a radial flow reactor. In the reactor, the catalyst moves slowly from top to bottom while the reaction gas mixture flows radially. This procedure is applied, for example, in the UOP-Oleflex dehydrogenation process. Since the reactors in this process are operated virtually adiabatically, it is advantageous to operate a plurality of reactors connected in series as a battery (typically up to four). This allows excessively large differences in the temperatures of the reaction gas mixture at the reactor entrance and at the reactor exit to be avoided (in the adiabatic mode of operation, the starting reaction gas mixture functions as a heat carrier, upon whose heat content the drop in the reaction temperature is dependent) and nevertheless allows attractive overall conversions to be achieved.

When the catalyst bed has left the moving bed reactor, it is fed to the regeneration and subsequently reused. The dehydrogenation catalyst used for this process may be, for example, a spherical dehydrogenation catalyst which consists substantially of platinum on spherical aluminum oxide support. In the UOP variant, hydrogen is added to the saturated hydrocarbon H (e.g. propane) to be dehydrogenated, in order to avoid premature catalyst aging. The working pressure is typically from 2 to 5 atm. The (molar) hydrogen to propane ratio is advantageously from 0.1 to 1. The reaction temperatures are preferably from 550 to 650° C. and the contact time of the catalyst with reaction gas mixture is selected from about 2 to 6 $h^{-1}$.

In the fixed bed processes described, the catalyst geometry may likewise be spherical, but also cylindrical (hollow or solid) or have a different geometry.

A further process variant for the heterogeneously catalyzed dehydrogenation of saturated hydrocarbons H described by Proceedings De Witt, Petrochem. Review, Houston, Tex., 1992 a, N1 is the possibility of a heterogeneously catalyzed dehydrogenation in a fluidized bed without diluting the hydrocarbon.

According to the invention, it is possible, for example, to operate two fluidized beds in parallel, of which one may be in the state of regeneration from time to time without negative effects on the overall process. The active composition used is chromium oxide on aluminum oxide. The working pressure is typically from 1 to 2 atm and the dehydrogenation temperature is generally from 550 to 600° C. The heat required for the dehydrogenation is introduced into the reaction system by preheating the dehydrogenation catalyst to the reaction temperature. The abovementioned dehydrogenation method is known in the literature as the Snamprogetti-Yarsintez process.

Alternatively to the procedures described above, the heterogeneously catalyzed dehydrogenation may also be realized with substantial exclusion of oxygen by a process developed by ABB Lummus Crest (see Proceedings De Witt, Petrochem. Review, Houston, Tex., 1992, P1).

Common to the heterogeneously catalyzed dehydrogenation processes of a saturated hydrocarbon H with substantial exclusion of oxygen described hitherto is that they are operated at saturated hydrocarbon H (e.g. propane) conversions of $\geq 30$ mol % (generally $\geq 60$ mol %) (based on single reaction zone pass). It is advantageous according to the invention that it is sufficient to achieve a saturated hydrocarbon H (e.g. propane) conversion of from $\geq 5$ mol % to $\leq 30$ mol % or $\leq 25$ mol %. This means that the heterogeneously catalyzed dehydrogenation may also be operated at conversions of from 10 to 20 mol % (the conversions are based on single reaction zone pass). Among other factors, this is based on the remaining amount of unconverted saturated hydrocarbon H (e.g. propane) functioning substantially as an inert diluent gas in the subsequent at least one partial oxidation and/or partial ammoxidation and later being recycled substantially without loss into the dehydrogenation zone and/or into the at least one partial zone.

For the realization of the abovementioned conversions, it is advantageous to carry out the heterogeneously catalyzed dehydrogenation at a working pressure of from 0.3 to 3 atm. It is further advantageous to dilute the saturated hydrocarbon H to be dehydrogenated under heterogeneous catalysis with steam. For instance, the heat capacity of the water on the one hand enables a portion of the effect of the endothermicity of the dehydrogenation to be compensated for and, on the other hand, the dilution with steam reduces the partial reactant and product pressure, which has a beneficial effect on the equilibrium location of the dehydrogenation. The use of steam, as already mentioned, also has an advantageous effect on the on-stream time of noble metal-containing dehydrogenation catalysts. If required, molecular hydrogen may also be added as a further constituent. The molar ratio of molecular hydrogen to saturated hydrocarbon H (e.g. propane) is generally $\leq 5$. The molar ratio of steam to saturated hydrocarbon H at a comparative low saturated hydrocarbon H conversion may therefore be from $\geq 0$ to 30, advantageously from 0.1 to 2 and favorably from 0.5 to 1. It also proves to be advantageous for a procedure with low propane conversion that only a comparatively small amount of heat is consumed on single reactor pass of the reaction gas and that comparatively low reaction temperatures are sufficient for achieving the conversion on single reactor pass.

It may therefore be appropriate to carry out the dehydrogenation with comparatively low propane conversion (virtually) adiabatically. This means that the starting reaction gas mixture will generally initially be heated to a temperature of from 500 to 700° C. (or from 550 to 650° C.) (for example by direct firing of the wall surrounding it). Normally, a single adiabatic pass through a catalyst bed will then be sufficient in order to achieve the desired conversion, and the reaction gas mixture will cool by from about 30° C. to 200° C. (depending on conversion and dilution). The presence of steam as a heat carrier is also noticeably advantageous from the point of view of an adiabatic method. The lower reaction temperature allows longer on-stream times of the catalyst bed used.

In principle, the heterogeneously catalyzed dehydrogenation with comparatively low conversion, whether conducted adiabatically or isothermally, can be carried out either in a fixed bed reactor or else in a moving bed or fluidized bed reactor.

Remarkably, to realize the process according to the invention, especially in adiabatic operation, a single shaft furnace reactor which is flowed through by the reaction gas mixture axially and/or radially is sufficient as a fixed bed reactor.

In the simplest case, this is a single closed reaction volume, for example a vessel, whose internal diameter is from 0.1 to 10 m, possibly also from 0.5 to 5 m, and in which the fixed catalyst bed is applied to a support device (for example a grid). The reaction volume which is charged with catalyst and heat-insulated in adiabatic operation is flowed through axially by the hot, saturated hydrocarbon H-containing reaction gas. The catalyst geometry may be either spherical or else annular or strand-shaped. Since the reaction volume can be realized in this case by a very inexpensive apparatus, preference is given to all catalyst geometries which have a particularly low pressure drop. These are in particular catalyst geometries which lead to a large cavity volume or are structured, for example monoliths or honeycombs. To realize a radial flow of the saturated hydrocarbon H-containing reaction gas, the reactor may, for example, consist of two concentric cylindrical grids disposed in a shell and the catalyst bed may be arranged in the annular gap. In the adiabatic case, the metal shell would in turn be thermally insulated.

Useful catalyst charges for a heterogeneously catalyzed dehydrogenation with comparatively low conversion on a single pass are in particular the catalysts disclosed in DE-A 199 37 107, in particular all of those disclosed by way of example.

After a prolonged operating time, the abovementioned catalysts can be regenerated in a simple manner, for example, by initially passing air (preferably) diluted with nitrogen and/or steam in first regeneration stages over the catalyst bed at an entrance temperature of from 300 to 600° C., frequently from 400 to 550° C. The gas hourly space velocity of regeneration gas may be, for example, from 50 to 10000 $h^{-1}$ and the oxygen content of the regeneration gas may be from 0.5 to 20% by volume.

In subsequent further regeneration stages, the regenerating gas used under otherwise identical regeneration conditions may be air. From an application point of view, it is advantageous to flush the catalyst with inert gas (for example $N_2$) before its regeneration.

It is generally to be recommended to subsequently regenerate with pure molecular hydrogen or with molecular hydrogen diluted with inert gas (preferably steam) (the hydrogen content should be $\geq 1\%$ by volume) under otherwise identical conditions.

The heterogeneously catalyzed dehydrogenation with comparatively low conversion ($\leq 30$ mol %) may in all cases be carried out at the same gas hourly space velocities (with regard both to the reaction gas overall and to the saturated hydrocarbon H contained in it) as the variants with high conversion (>30 mol %). This gas hourly space velocity of reaction gas may be, for example, from 100 to 10000 $h^{-1}$, frequently from 300 to 5000 $h^{-1}$, i.e. in many cases from about 500 to 3000 $h^{-1}$.

In a particularly elegant manner, the heterogeneously catalyzed dehydrogenation with comparatively low conversion can be realized in a tray reactor.

This comprises more than one catalyst bed catalyzing the dehydrogenation in spatial succession. The catalyst bed number may be from 1 to 20, advantageously from 2 to 8, or else from 3 to 6. The catalyst beds are preferably arranged in radial or axial succession. From an application point of view, it is appropriate to use the fixed bed catalyst type in such a tray reactor.

In the simplest case, the fixed catalyst beds in a shaft furnace reactor are arranged axially or in the annular gaps of concentric cylindrical grids. However, it is also possible to arrange the annular gaps in segments above one another and to conduct the gas after it has passed radially through one segment into the next segment above it or below it.

Appropriately, the reaction gas mixture will be subjected to intermediate heating in the tray reactor on its way from one catalyst bed to the next catalyst bed, for example by passing it over heat exchanger ribs heated by hot gases or by passing it through pipes heated by hot combustion gases.

When the tray reactor is otherwise operated adiabatically, it is sufficient for the desired conversions (≦30 mol %), especially when using the catalysts described in DE-A 199 37 107, especially those of the exemplary embodiments, to conduct the reaction gas mixture into the dehydrogenation reactor preheated to a temperature of from 450 to 550° C. and to keep it within this temperature range inside the tray reactor. This means that the entire dehydrogenation can thus be realized at very low temperatures, which is particularly advantageous for the on-stream time of the fixed catalyst beds between two regenerations.

It is even more beneficial to carry out the above-outlined intermediate heating in a direct way (autothermal method). To this end, a limited amount of molecular oxygen is added to the reaction gas mixture either before it flows through the first catalyst bed and/or between the subsequent catalyst beds. Depending on the dehydrogenation catalyst used, a limited combustion of the hydrocarbons contained in the reaction gas mixture, any coke or coke-like compounds already deposited on the catalyst surface and/or hydrogen formed in the course of the heterogeneously catalyzed dehydrogenation and/or added to the reaction gas mixture is thus effected (it may also be advantageous from an application point of view to introduce catalyst beds in the tray reactor which are charged with catalyst which specifically (selectively) catalyzes the combustion of hydrogen (and/or of hydrocarbon) (examples of useful catalysts include those of the documents U.S. Pat. No. 4,788,371, U.S. Pat. No. 4,886,928, U.S. Pat. No. 5,430,209, U.S. Pat. No. 5,530,171, U.S. Pat. No. 5,527,979 and U.S. Pat. No. 5,563,314; for example, such catalyst beds may be accommodated in the tray reactor in alternation to the beds containing dehydrogenation catalyst)). The heat of reaction released thus allows virtually isothermal operation of the heterogeneously catalyzed propane dehydrogenation in a virtually autothermal manner. As the selected residence time of the reaction gas in the catalyst bed is increased, dehydrogenation is thus possible at decreasing or substantially constant temperature, which allows particularly long on-stream times between two regenerations.

In general, oxygen feeding as described above should be carried out in such a manner that the oxygen content of the reaction gas mixture, based on the amount of saturated hydrocarbon H contained therein, is from 0.5 to 30% by volume. Useful oxygen sources include both pure molecular oxygen and oxygen diluted with inert gas, for example CO, $CO_2$, $N_2$ or noble gases, but in particular also air. The resulting combustion gases generally have an additional dilution effect and thus support heterogeneously catalyzed dehydrogenation.

The isothermicity of the heterogeneously catalyzed dehydrogenation can be further improved by incorporating closed (for example tubular) internals which have advantageously, but not necessarily, been evacuated before filling in the spaces between the catalyst beds in the tray reactor. Such internals may also be placed in each catalyst bed. These internals contain suitable solids or liquids which evaporate or melt above a certain temperature, thereby consuming heat, and, when the temperature falls below this value, condense again and thereby release heat.

Another possible method of heating the starting reaction gas mixture for the heterogeneously catalyzed dehydrogenation to the required reaction temperature involves combusting a portion of the saturated hydrocarbon H and/or $H_2$ contained therein by means of molecular oxygen (for example over suitable specific combustion catalysts, for example by simply passing over and/or through) and to effect the heating to the desired reaction temperature by means of the heat of combustion released in this manner. The resulting combustion products, such as $CO_2$ and $H_2O$, and also any $N_2$ accompanying the molecular oxygen required for the combustion advantageously constitute inert diluent gases.

The abovementioned hydrogen combustion can be particularly elegantly realized as described in DE-A 10211275. This is a process for continuously partially dehydrogenating saturated hydrocarbon H in the gas phase under heterogeneous catalysis by continuously feeding a reaction gas containing the saturated hydrocarbon H to be dehydrogenated to a reaction zone, conducting the reaction gas in the reaction zone over at least one fixed catalyst bed, over which molecular hydrogen and at least partially dehydrogenated hydrocarbon H are formed by catalytic dehydrogenation, adding at least one molecular oxygen-containing gas to the reaction gas before and/or after entry into the reaction zone, partially oxidizing the molecular oxygen in the molecular hydrogen contained in the reaction gas in the reaction zone to give steam and withdrawing a product gas from the reaction zone which comprises molecular hydrogen, steam, partially dehydrogenated hydrocarbon H and saturated (to be dehydrogenated) hydrocarbon, which comprises dividing the product gas removed from the reaction zone into two portions of identical composition and recycling one of the two portions as cycle gas into the dehydrogenation reaction zone and further using the other portion as product gas mixture A in accordance with the invention.

The above-described variants of the catalytic dehydrogenation to be employed in accordance with the invention can be employed in particular when the saturated hydrocarbon H to be dehydrogenated is propane and/or isobutane.

The product gas mixture A and/or the product gas mixture A' to be obtained from it as described can then be used in a manner known per se to charge a heterogeneously catalyzed partial oxidation and/or ammoxidation with a gas mixture B (cf. prior art cited at the outset). It is essential to the invention only that the product gas mixture A, the product gas mixture A' and/or the mixture B, before the at least one heterogeneously catalyzed partial oxidation and/or ammoxidation, is subjected to a mechanical separating operation by which solid particles present in these gas mixtures can be removed from these gas mixtures.

Useful partial oxidations for the process according to the invention are in particular the partial oxidation of propene (obtained by partial dehydrogenation of propane) to acrolein and/or acrylic acid and the partial oxidation of isobutene (obtained by partial dehydrogenation of isobutane) to methacrolein and/or methacrylic acid.

Useful partial ammoxidations for the process according to the invention are in particular the partial ammoxidation of propene to acrylonitrile and also the partial ammoxidation of isobutene to methacrylonitrile.

EXAMPLE

1. Dehydrogenation Catalyst

In a similar manner to that described in DE-A 10219879, a Pt/Sn alloy which had been promoted with the elements Cs, K and La in oxidic form was applied to the external and internal surface of $ZrO_2.SiO_2$ mixed oxide supports (extrudates of a length in the range from 3 to 8 mm and a diameter of 2 mm; prepared according to example 3 of DE-A 10219879). The elemental stoichiometry (mass ratio) was: $Pt_{0.3}Sn_{0.6}La_{3.0}Cs0.5K_{0.2}(ZrO_2)_{88.3}(SiO_2)_{7.1}$.

The alloy promoted as described was applied by saturating the spalled support with salt solutions of the appropriate metals and subsequent thermal treatments (1.5 h) at 560° C. in an air stream. In the course of the thermal treatment, both the active components Pt and Sn and the promoters were converted to their oxidic form. In the dehydrogenation reactor described hereinbelow, the active components of the catalyst precursor were reduced to the metals as described hereinbelow in a hydrogen stream at 500° C. to obtain the active catalyst.

2. Dehydrogenation Reactor (C330)

650 ml (762 g) of the catalyst precursor obtained as described above were used to charge a vertical tubular reactor (tube length: 2049 mm, wall thickness: 7 mm, internal diameter: 41 mm, material: internally alonized (i.e. aluminum oxide-coated) steel tube) as follows (from bottom to top, supported on a catalyst base):
299 mm rings of steatite (external diameter×length×internal diameter=7 mm×3 mm×4 mm), then 50 mm steatite spheres of diameter 4-5 mm, then 25 mm steatite spheres of diameter 1.5-2.5 mm, then 500 mm catalyst precursor, then 50 mm steatite spheres of diameter 4-5 mm, then 1080 mm rings of steatite (external diameter×length×internal diameter=7 mm×3 mm×4 mm). The steatite used was steatite C-220 from CeramTec. The reaction tube was heated (electrically) by means of a heating coil furnace from HTM Reetz (into which the reaction tube was introduced) in four immediately successive heating zones from bottom to top, of which each extends to a length of 2×220 cm. Between the tube surface and the heating coils was an air gap of approx. 72.5 mm width. From bottom to top, the reaction tube was coated to a length of 1000 mm on its external wall with a microporous insulating material of the MPS-Super G type from Mientherm, DE and the layer thickness of 100 mm (quasi-adiabatic reaction part). In this region, the heating functioned merely as support heating, while it served to directly heat the tube section in the upper region.

From top to bottom, a thermowell was introduced, centered in the reaction tube, to a length of 1.50 m (external diameter=6 mm, internal diameter=4 mm) to accommodate a plurality of thermal elements.

From bottom to top, a thermowell of length 60 cm was introduced into the reaction tube in a corresponding manner.

The catalyst precursor was activated in a hydrogen stream as in example 1 of DE-A 10211275.

3. Experimental Plant

The hydrocarbon to be dehydrogenated under heterogeneous catalysis which was used was propane or n-butane (referred to below as liquefied petroleum gas=LPG).

The experimental plant was composed of 4 parts:
metering unit;
reactor unit;
cycle gas unit; and
discharge unit.

In the metering unit, the liquid starting materials LPG and water (if required in a nitrogen stream) were passed through an evaporator W100 and converted to the gas phase therein. Downstream of the evaporator, if required, air, molecular oxygen and molecular hydrogen could be admixed to the gas mixture generated in the evaporator to obtain the desired fresh starting mixture.

In the reactor unit, the fresh starting mixture (optionally in a mixture with cycle gas) was heated in a preheater (heat exchanger) W200 to a temperature of from 400 to 500° C. and subsequently conducted into the dehydrogenation reactor C330 described (from top to bottom). The heating zones, from top to bottom, had the following temperatures: 500° C., 550° C., 550° C. and 550° C. The inlet pressure into the dehydrogenation reactor which was selected was 2 bar.

The product gas mixture A leaving the dehydrogenation reactor was conducted through an air-cooled heat exchanger and cooled to 300° C. Subsequently, it was passed fully or partly into the discharge part via a directing tube and further processed therein. When only a portion of the cooled product gas mixture A had been conducted into the discharge part, the remaining portion was fed to the cycle gas unit.

In the cycle gas unit, the portion of the product gas mixture A which had been recycled was cooled further initially to 150° C. in a heat exchanger W420 operated with heat carrier oil, then recompressed to 2 bar in a compressor V440 and then, after passing through a heat exchanger W460, where it was heated to 300° C., upstream of the preheater W200, combined with fresh starting gas mixture (and then fed to the preheater).

4. Results

The experimental plant was operated substantially continuously over a period of 3 months. In total, 26 reaction cycles were carried out. After each reaction cycle, a regeneration of the dehydrogenation catalyst in accordance with DE-A 10028582 was carried out with the sequence of purging, burning off, purging, reducing. Within a reaction cycle (the shortest duration of a reaction cycle was 3 h and the longest duration of a reaction cycle was 100 h), the conditions were kept constant. The conditions of all cycles were within the following framework:

| | |
|---|---|
| hydrocarbon: | LPG; |
| cycle duration: | 3-100 h; |
| LPG amount: | 500-2000 g/h; |
| fresh steam: | 500-1000 g/h; |
| nitrogen: | 0-50 l (STP)/h; |
| air: | 0-375 l (STP)/h; |
| hydrogen: | 0-150 l (STP)/h; |
| temperature of the heating zones: | 500° C., 550° C., 550° C. and 550° C.; |
| inlet pressure: | 2 bar |
| cycle gas ratio: | 0 or 5 (ratio of amount recycled to amount discharged) |

The parts of the experimental plant which had been exposed to temperatures of up to 300° C. were manufactured from V2A steel. The parts of the experimental plant which were exposed to temperatures above 300° C. were manufactured from 1.4841 steel.

On completion of the experimental series, flash rust was detected in considerable amounts in all parts of the experimental plant which had been flowed through by cycle gas and by product gas mixture A. Its original cause was rusting of the guide tube in which water had condensed out (apparently caused by the preceding cooling of the product gas mixture A).

The analysis of the flash rust by means of atomic absorption spectroscopy, in addition to the expected constituents Fe, Ni and Cr, also revealed proportions of Zr, Si and Pt which could only stem from the dehydrogenation catalyst. Overall, the analyzed rust sample exhibited the following element amounts:

| | |
|---|---|
| carbon: | 1.5 g/100 g; |
| Al: | 2.2 g/100 g; |
| Cr: | 2.6 g/100 g; |
| Fe: | 13.1 g/100 g; |
| Mg: | 10.6 g/100 g; |
| Ni: | 1.9 g/100 g; |
| Pt: | 0.019 g/100 g; |
| Si: | 20.6 g/100 g; |
| Zr: | 0.17 g/100 g. |

In an analysis of a randomly taken sample of product gas mixture A, Zr, Si and Pt could not be detected. Apparently, the amounts present are below the detection limit.

We claim:

1. A process for preparing at least one partial oxidation and/or ammoxidation product of hydrocarbon by subjecting at least one saturated hydrocarbon H to heterogeneously catalyzed dehydrogenation in the gas phase to form a product gas mixture A which comprises at least one partially dehydrogenated hydrocarbon H, leaving constituents present in the product gas mixture A, other than the saturated hydrocarbon H and other than the partially dehydrogenated hydrocarbon H therein, or partly or fully removing them to obtain a product gas mixture A', and subjecting product gas mixture A and/or product gas mixture A', as a constituent of a gas mixture B, to at least one heterogeneously catalyzed partial oxidation and/or ammoxidation of the at least one partially dehydrogenated hydrocarbon H present in the product gas mixture A and/or product gas mixture A', which comprises subjecting the product gas mixture A, the product gas mixture A' and/or the gas mixture B, before the at least one heterogeneously catalyzed partial oxidation and/or ammoxidation, to at least one mechanical separating operation by which solid particles present in these gas mixtures are removed.

2. A process as claimed in claim 1, wherein the saturated hydrocarbon H is propane, and the heterogeneously catalyzed partial oxidation of the partially dehydrogenated hydrocarbon H is the partial oxidation of propene to acrolein and/or acrylic acid.

3. A process as claimed in claim 1, wherein the saturated hydrocarbon H is isobutane, and the heterogeneously catalyzed partial oxidation of the partially dehydrogenated hydrocarbon H is the partial oxidation of isobutene to methacrolein and/or methacrylic acid.

4. A process as claimed in claim 1, wherein the saturated hydrocarbon H is propane, and the heterogeneously catalyzed partial ammoxidation of the partially dehydrogenated hydrocarbon H is the partial ammoxidation of propene to acrylonitrile.

5. A process as claimed in claim 1, wherein the saturated hydrocarbon H is isobutane, and the heterogeneously catalyzed partial ammoxidation of the partially dehydrogenated hydrocarbon H is the partial ammoxidation of isobutene to methacrylonitrile.

6. A process as claimed in claim 1, wherein constituents present in the product gas mixture A, other than the saturated hydrocarbon H and other than the partially dehydrogenated hydrocarbon H therein, are partly or fully removed to obtain a product gas mixture A'.

7. A process as claimed in claim 1, comprising subjecting product gas mixture A and/or product gas mixture A', as a constituent of a gas mixture B, to at least one heterogeneously catalyzed partial oxidation of the at least one partially dehydrogenated hydrocarbon H present in the product gas mixture A and/or product gas mixture A'.

8. A process as claimed in claim 1, comprising subjecting product gas mixture A and/or product gas mixture A', as a constituent of a gas mixture B, to at least one heterogeneously catalyzed partial ammoxidation of the at least one partially dehydrogenated hydrocarbon H present in the product gas mixture A and/or product gas mixture A'.

9. A process as claimed in claim 1, comprising subjecting product gas mixture A and/or product gas mixture A', as a constituent of a gas mixture B, to at least one heterogeneously catalyzed partial oxidation and ammoxidation of the at least one partially dehydrogenated hydrocarbon H present in the product gas mixture A and/or product gas mixture A'.

10. A process as claimed in claim 6, comprising subjecting product gas mixture A and/or product gas mixture A', as a constituent of a gas mixture B, to at least one heterogeneously catalyzed partial oxidation of the at least one partially dehydrogenated hydrocarbon H present in the product gas mixture A and/or product gas mixture A'.

11. A process as claimed in claim 6, comprising subjecting product gas mixture A and/or product gas mixture A', as a constituent of a gas mixture B, to at least one heterogeneously catalyzed partial ammoxidation of the at least one partially dehydrogenated hydrocarbon H present in the product gas mixture A and/or product gas mixture A'.

12. A process as claimed in claim 6, comprising subjecting product gas mixture A and/or product gas mixture A', as a constituent of a gas mixture B, to at least one heterogeneously catalyzed partial oxidation and ammoxidation of the at least one partially dehydrogenated hydrocarbon H present in the product gas mixture A and/or product gas mixture A'.

13. A process as claimed in claim 7, wherein the saturated hydrocarbon H is propane, and the heterogeneously catalyzed partial oxidation of the partially dehydrogenated hydrocarbon H is the partial oxidation of propene to acrolein and/or acrylic acid.

14. A process as claimed in claim 7, wherein the saturated hydrocarbon H is isobutane, and the heterogeneously catalyzed partial oxidation of the partially dehydrogenated hydrocarbon H is the partial oxidation of isobutene to methacrolein and/or methacrylic acid.

15. A process as claimed in claim 8, wherein the saturated hydrocarbon H is propane, and the heterogeneously catalyzed partial ammoxidation of the partially dehydrogenated hydrocarbon H is the partial ammoxidation of propene to acrylonitrile.

16. A process as claimed in claim 8, wherein the saturated hydrocarbon H is isobutane, and the heterogeneously catalyzed partial ammoxidation of the partially dehydrogenated hydrocarbon H is the partial ammoxidation of isobutene to methacrylonitrile.

17. A process as claimed in claim 10, wherein the saturated hydrocarbon H is propane, and the heterogeneously catalyzed partial oxidation of the partially dehydrogenated hydrocarbon H is the partial oxidation of propene to acrolein and/or acrylic acid.

18. A process as claimed in claim 10, wherein the saturated hydrocarbon H is isobutane, and the heterogeneously catalyzed partial oxidation of the partially dehydrogenated hydrocarbon H is the partial oxidation of isobutene to methacrolein and/or methacrylic acid.

19. A process as claimed in claim 11, wherein the saturated hydrocarbon H is propane, and the heterogeneously catalyzed partial ammoxidation of the partially dehydrogenated hydrocarbon H is the partial ammoxidation of propene to acrylonitrile.

20. A process as claimed in claim 11, wherein the saturated hydrocarbon H is isobutane, and the heterogeneously catalyzed partial ammoxidation of the partially dehydrogenated hydrocarbon H is the partial ammoxidation of isobutene to methacrylonitrile.

21. A process as claimed in claim 1, wherein the dehydrogenation catalyst is at least one metal deposited on a support.

22. A process as claimed in claim 1, wherein the catalytic dehydrogenation is conducted under a working pressure ranging from 0.3 to 3 atm.

23. A process as claimed in claim 22, wherein the catalytic dehydrogenation is conducted in the presence of steam.

* * * * *